United States Patent [19]

Hsu

[11] Patent Number: 4,479,496

[45] Date of Patent: Oct. 30, 1984

[54] ACUPUNCTURE NEEDLE AND NEEDLE GUIDE ASSEMBLY

[76] Inventor: John J. Hsu, 7224 Old Mill Rd., Birmingham, Mich. 48010

[21] Appl. No.: 370,682

[22] Filed: Apr. 22, 1982

[51] Int. Cl.$^3$ .............................................. A61B 17/34
[52] U.S. Cl. ................................................ 128/329 A
[58] Field of Search ............... 128/329 R, 329 A, 314, 128/315, 361; 604/46, 199, 22

[56] References Cited

U.S. PATENT DOCUMENTS

| | | | |
|---|---|---|---|
| 2,857,912 | 10/1958 | Feinstone et al. | 604/199 |
| 3,875,944 | 4/1975 | Toyama | 128/303.1 |
| 3,905,375 | 9/1975 | Toyama | 128/329 A |
| 3,943,932 | 3/1976 | Woo | 128/329 A |
| 3,957,053 | 5/1976 | Woo | 128/329 A |
| 4,139,011 | 2/1979 | Benoit et al. | 128/329 A |
| 4,154,342 | 5/1979 | Wallace | 604/199 |
| 4,161,943 | 7/1979 | Nogier | 128/329 A |
| 4,262,672 | 4/1981 | Kief | 128/329 A |

Primary Examiner—Dalton L. Truluck
Assistant Examiner—Michelle N. Lester
Attorney, Agent, or Firm—Gifford, VanOphem, Sheridan, Sprinkle & Nabozny

[57] ABSTRACT

A needle having an enlarged diameter handle is encased within a tubular housing having a reduced diameter bore portion which engages a portion of the handle. A second portion of the handle extends outwardly from the housing and is enclosed in a removable end cap secured over that end of the housing. The other end of the housing encloses the needle and includes a second end cap removably secured to the second end of the tubular housing.

16 Claims, 7 Drawing Figures

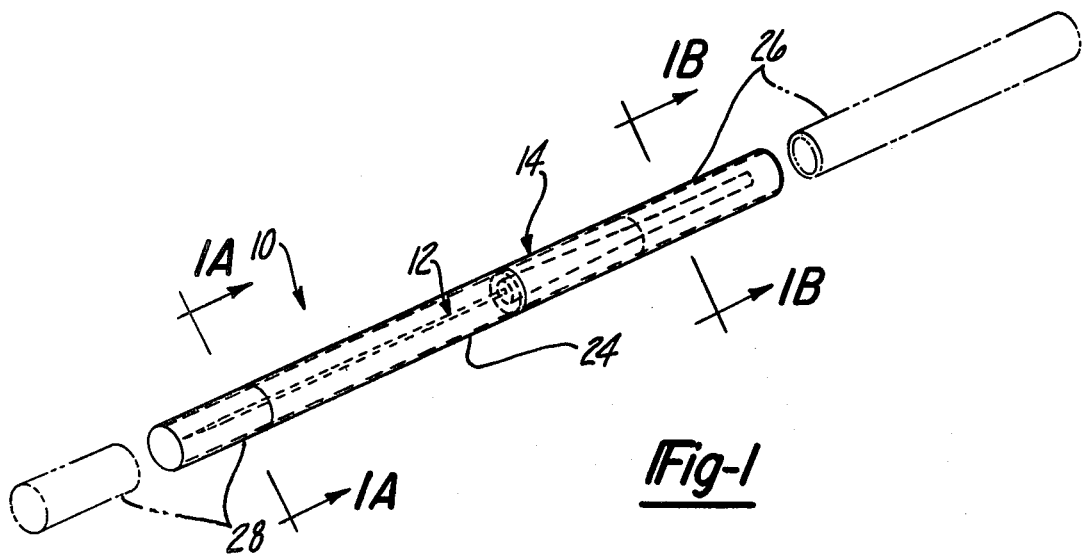
*Fig-1*
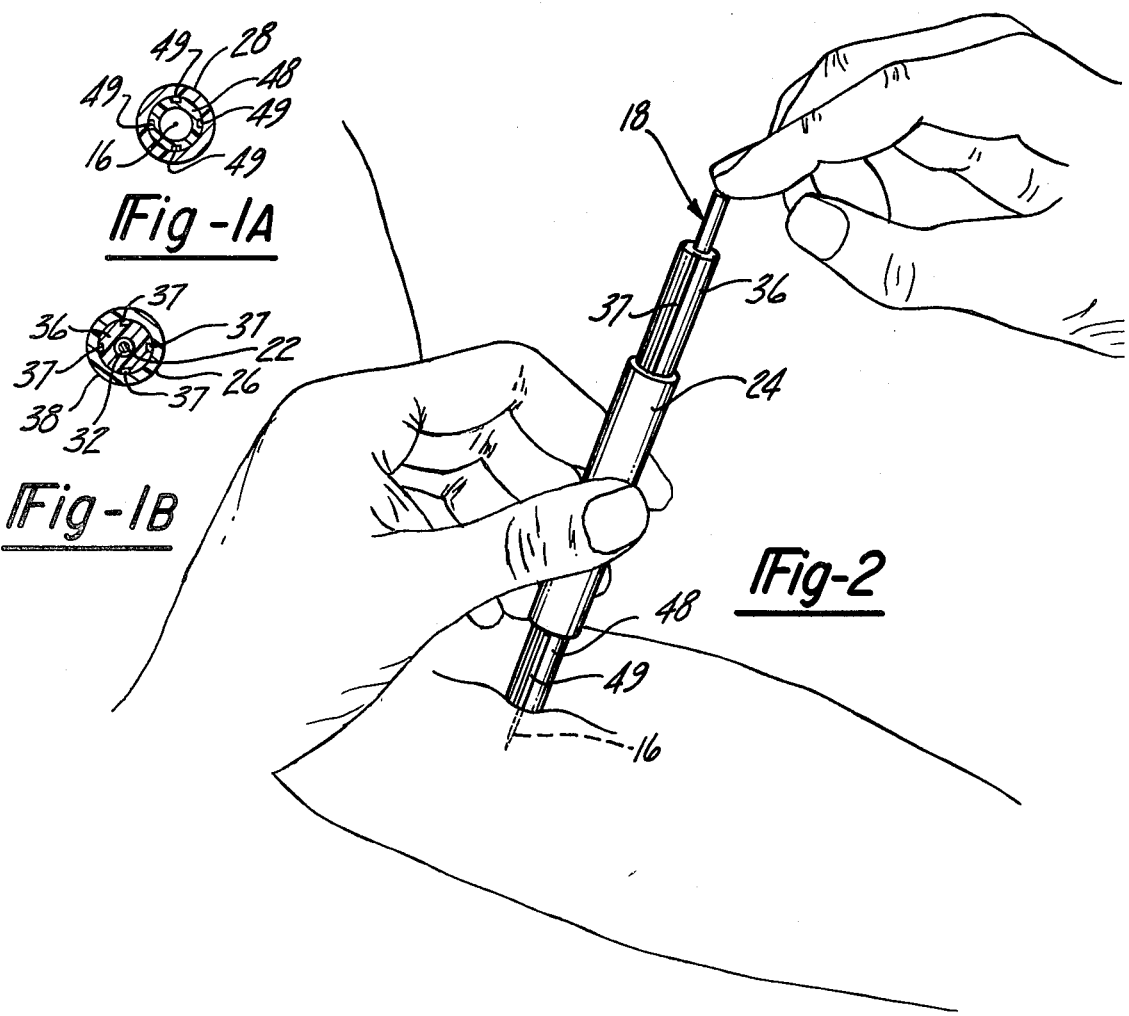
*Fig-1A*
*Fig-1B*
*Fig-2*

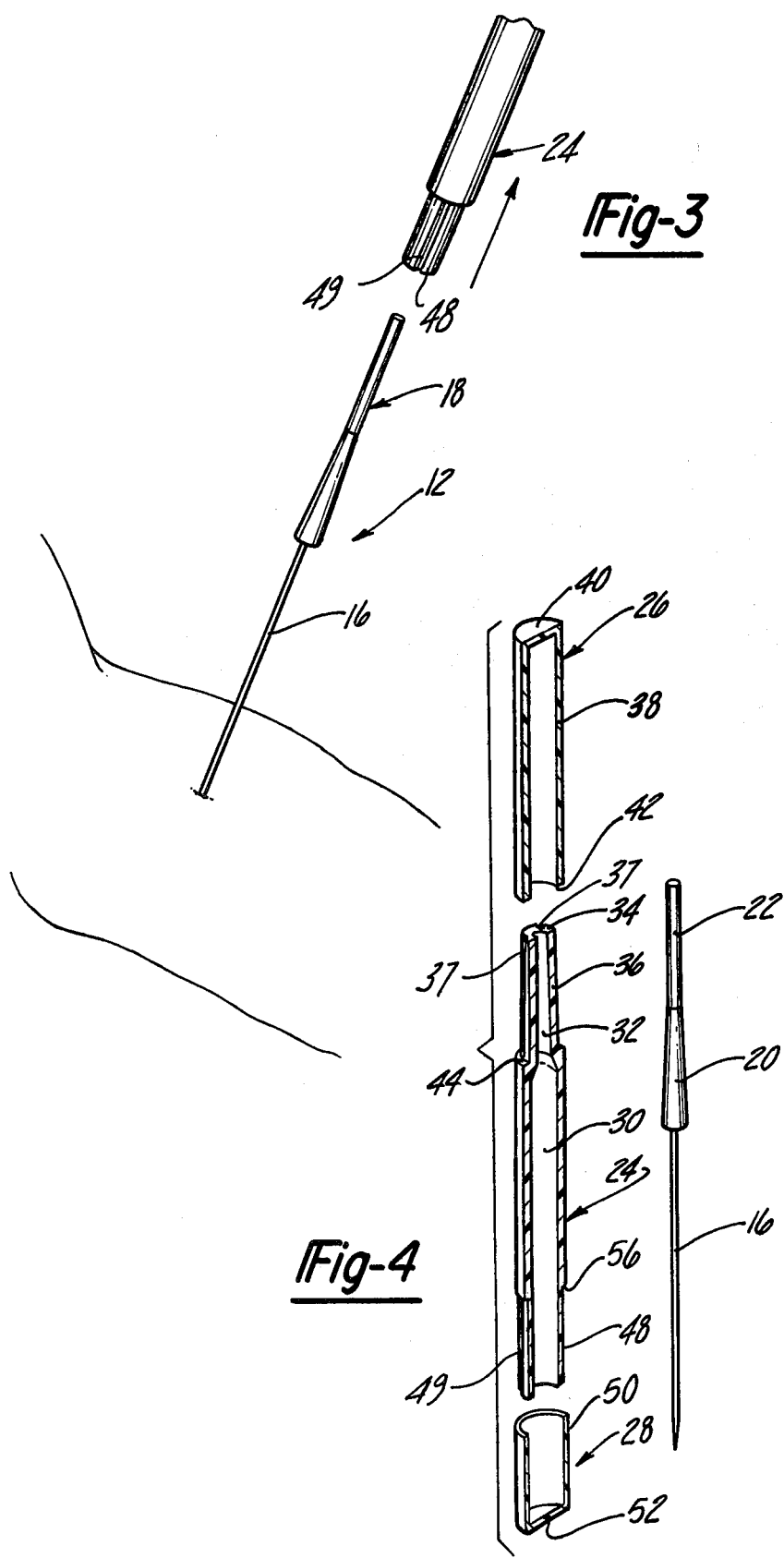

ACUPUNCTURE NEEDLE AND NEEDLE GUIDE ASSEMBLY

BACKGROUND OF THE INVENTION

I. Field of the Invention

The present invention relates generally to medical devices for puncturing the skin and more particularly to an acupuncture needle and applicator therefor which provides accurate placement of the needle, maintains the sterility of the needle before insertion into the skin, and is readily removable from the placed needle.

II. Description of the Prior Art

Acupuncture has gained increasing acceptance as a medical treatment. The treatment involves the insertion of needles into the skin of a patient at various areas of the body. Typically, the needles are filiform structures, having a length sufficient to permit a portion of the needle to be embedded in the skin to a depth sufficient to reach the area to be treated and a portion which remains protruded from the skin so that the needle can be removed when the treatment is completed. While these filiform needles can be inserted by skillful hands without additional aid, and can be sterilized to reduce the risk of infection by contamination of the needles, they require extreme care to be protected from contamination before and during their use. Moreover, due to the extremely small diameter and relative long length of these needles, insertion and rotation of the needles by hand can be difficult.

In order to overcome these disadvantages, applicators have been developed which encase the needle and provide a mechanism for releasing the needle from the applicator and inserting it into the skin. One of the previously known types of applicators includes a plunger mechanism for projecting the needle from the enclosure. Such a structure employs numerous parts and thus is quite complicated and expensive to produce.

Another known type of projector applicator is disclosed in U.S. Pat. No. 3,905,375 to Toyama. That patent discloses a needle having an enlarged diameter shank portion which is encased in a pair of tubular members. The ends of the first tube are enclosed by rupturable membranes, and the tube is slidably insertable into the second tube. The second tube has a closed end which abuts against the axial end of the shank of the needle. To discharge the needle, the second tube is depressed over the first tube so as to urge the needle through the rupturable membranes toward the skin of the patient. However, such a device is disadvantageous for the reason that during handling or transportation, the outer tube can be inadvertently depressed over the inner tube and cause the needle to protrude through the rupturable membrane and become exposed after sterilization. More importantly, since both the needle and the shank of the needle must pass through the membrane, in order to remove the applicator from the needle, portions of the membrane may contaminate the site of insertion of the needle. The open end of the shield may not adequately protect the needle from contamination. The ruptured membrane can cause friction between the handle and the shield during the insertion and removal of the shield and plunger assembly and can possibly pull the needle out of the stem during the process of removal of the assembly.

SUMMARY OF THE PRESENT INVENTION

The present invention overcomes the above-mentioned disadvantages by providing an acupuncture needle and needle quide assembly including a filiform needle having an enlarged diameter handle, together with a tubular housing having a bore portion at one end which slidably receives a portion of the handle of the needle. The bore portion of the tube supports the needle within a needle enclosing chamber formed by a second bore portion on one side of the first bore portion, while a portion of the handle extends outwardly from the other side of the first bore portion. The open ends of the tubular housing are enclosed by removable caps, one end cap including a chamber enclosing the extended portion of the handle.

Preferably, the ends of the tubular member include reduced diameter portions which are slidably receivable in the end caps and which form an abutment surface against which the end of the end cap can rest. In addition, it is preferable that the first bore portion include means for limiting sliding displacement of the handle in a direction away from the second bore portion, and this can be conveniently accomplished by tapering the first bore portion.

The needle and needle guide assembly can be placed as a unit in an autoclave in order to sterilize the entire structure. Once the structure has been sterilized, the needle remains enclosed within the case until needed for use. When the end caps are removed from the tubular member, the needle remains enclosed in the chamber formed by the second bore portion while only a portion of the handle extends outwardly from the housing. The handle can be tapped so that the handle slides through the first bore portion and into the second bore portion, thereby driving the needle into the skin of the patient. The enlarged diameter of the handle enables the needle to be easily manipulated and accurately positioned into the desired locus. Once the needle has been placed, the tube is easily pulled away and removed from the needle.

Thus, it can be seen that the present invention avoids the need for the operator to contact the insertable portion of the needle, and avoids exposure of the insertable portion of the needle prior to insertion. Accordingly, the present invention provides an aseptic technique for performing acupuncture, improves the accuracy of applying the needle, especially at areas of the body which are difficult to treat, maintains the needle in perfect structural condition, and can reduce the discomfort felt by the patient during treatment.

BRIEF DESCRIPTION OF THE DRAWING

The present invention will be more clearly understood by reference to the following detailed description when read in conjunction with the accompanying drawing in which like reference characters refer to like parts throughout several views and in which:

FIG. 1 is a perspective view of the needle and needle guide assembly according to the present invention;

FIG. 1A is a cross section taken substantially along line 1A—1A in FIG. 1;

FIG. 1B is a cross section taken substantially along line 1B—1B of FIG. 1;

FIG. 2 is a further perspective view showing the device in FIG. 1 with the end caps removed and in position for use according to the present invention;

FIG. 3 is a still further perspective view of the the device shown in FIG. 2 in a further operative position;

FIG. 4 is an exploded sectional view of portions of the device according to the present invention; and FIG. 5 is a sectional view of the device shown in FIG. 1.

DETAILED DESCRIPTION OF THE PREFERRED EMBODIMENT OF THE PRESENT INVENTION

Referring first to FIG. 1, a needle and needle guide assembly 10 according to the present invention is thereshown comprising an acupuncture needle 12 encased within housing 14. As best shown in FIGS. 3 and 4, the needle 12 comprises a filiform needle 16 and a handle 18. The handle 18 comprises a conical portion 20 secured at one end of filiform needle 16 and a cylindrical portion 22 extending from the other axial end of the conical portion 20. Preferably, the needle 16 is securely fastened to the handle 18 by embedding the needle in the conical portion 20.

The handle 18 can be made in one piece and is, like the housing 14, made of a material which retains its shape when heated to sterilization temperatures in an autoclave. Preferably, the handle 18 and housing 14 are made of a nonallergenic plastic material. However, the handle could also be made of metal, wood or other suitable materials. In any event, it will be understood that the needle 16 is preferably made of stainless steel.

Referring now to FIGS. 1, 4 and 5, the housing 14 comprises a main tubular body 24 and removable end caps 26 and 28. The main tubular body housing 24 includes a central bore 30 having a diameter greater than the widest portion of the conical handle portion 20, and the wall of the tube forms a reduced diameter bore portion 32 at one end. The reduced diameter bore portion 32 substantially coincides with the shape of the conical handle portion 20. Accordingly, the reduced diameter bore portion 32 and conical handle portion 20 taper radially inwardly toward the end 34 of main body tubular housing 24 and the cylindrical handle portion 22, respectively. Consequently, the conical handle portion 20 can be wedged within the reduced diameter bore portion 32 and, therefore, retains the needle 16 within the chamber 30.

As best shown in FIGS. 4 and 5, the reduced diameter bore portion 32 coincides with a reduced diameter peripheral portion 36. The end cap 26 includes a tubular body portion 38 and an end wall 40. Tubular body portion 38 is slidably received over the reduced peripheral portion 36. The tubular portion 38 of the end cap 26 is substantially longer than the reduced diameter peripheral portion 36 of housing 24 so that when the end 42 of end cap 26 abuts against the abutment wall 44, the handle portion 22 is encased within the end cap 26 without being dislodged by the end wall 40 of the end cap 26, as is clearly shown in FIG. 5.

The lower end of housing 24 also includes a reduced diameter, peripheral portion 48 which slidably receives the end cap 28. The end cap 28 is similar to the end cap 26 and includes tubular portion 50 and an end wall 52. The tubular portion 50 of the end cap 28 is slightly longer than the reduced diameter peripheral portion 48 so that a slight space 54 is formed between the end of the housing 24 and the end wall 52 when the open end of the end cap 28 abuts against the abutment wall 56 on the housing 24. Since the chamber 30 is longer than the needle 16, it can be seen that the needle 16 is safely retracted from the end wall 52 of cap 28 and is, therefore, protected from being bent by inadvertent contact with a foreign object. Moreover, the space 54 as well as the grooves 37 and 49 which are best shown in FIGS. 1A and 1B enable air to communicate throughout the housing 14 as well as between the inside and the outside of the housing 14 during autoclave sterilization.

Having thus described the important structural features of the present invention, the operation of the needle and needle guide assembly 10 of the present invention is easily described. The assembled unit 10 is placed in an autoclave and heated to a sterilizing temperature. Both the inside and the outside of the assembly 10 are sterilized. The assembly 10 is then removed from the autoclave for storage and use.

When an operator desires to apply an acupuncture treatment, the end caps 26 and 28 are removed from the housing 24 as shown in phantom line in FIG. 1. The lower end of the housing 24 is then placed over a position on the patient's skin which is to be treated. It can be seen that needle 16 remains enclosed within the chamber 30 of the housing 24 while cylindrical portion 22 of the handle 18 is exposed exteriorly of the housing 24. As shown in FIG. 2, the handle 18 is tapped by the finger of the operator in order to drive the needle 16 into the acupuncture point of the patient's skin. Thus, the needle is embedded in the skin without exposure to, or contact with, any contaminating materials. Moreover, once the needle has been embedded in the skin in the desired position, the narrow end of the conical bore 32 engages cylindrical handle portion 22 to accurately guide the needle. While needle 16 can be easily manipulated into the skin because of the thick handle 18, the housing 24 is easily removed by sliding it over the handle 18 as shown in FIG. 3. The needle is then retained in position and manipulation of the needle 16 can be executed without interference with the housing 24. Any discomfort to the patient during treatment is alleviated by the quick thrust of the needle 16 into the skin with the aid of the housing 14 as a result of a tap on the handle 18.

As a result, it can be seen that the present invention provides a means for storing, transporting, and applying needles used in acupuncture treatment without subjecting the needle to exposure to, or contact with contaminating materials prior to insertion of the needle in the skin of the patient. The applicator also provides a convenient enclosure for protecting the needle as well as a means for guiding the needle into the proper position on the skin of the patient. Moreover, it will be understood that since the structure of the present invention is rather simple and does not require complicated assembly or components, the present invention provides a disposable apparatus which can be discarded after a single use.

Having thus described my invention, many modifications thereto will become apparent to those skilled in the art to which it pertains without departing from the scope and spirit of the present invention as defined in the appended claims.

What is claimed is:

1. An acupuncture needle and needle guide assembly comprising:
   a needle;
   an elongated handle having a first axial portion secured to one end of said needle;
   a tubular housing having a first bore portion appropriately dimensioned to frictionally engage said first portion of said handle, and a second elongated portion adjacent said first bore portion and dimensioned to enclose said needle therein;

first means for manually slidably displacing said handle in a direction toward said second portion of said housing; and second means for restricting displacement of said handle in a direction away from said second portion of said housing.

2. The invention as defined in claim 1 wherein said first means comprises a second axially extended portion of said handle secured to said first portion of said handle.

3. The invention as defined in claim 1 wherein said first bore portion is tapered radially inwardly in a direction away from said second portion of said housing and said first portion of said handle is correspondingly tapered.

4. The invention as defined in claim 2 and further comprising a tubular end cap having a central bore adapted to receive said second handle portion and removably received over the periphery of said first portion of said housing.

5. The invention as defined in claim 4 wherein said first portion of said housing is formed with a reduced peripheral cross-section to thereby define an abutment surface intermediate said first portion of said housing and said second portion of said housing, and wherein an axial end of said end cap rests against said abutment surface.

6. The invention as defined in claim 1 and further comprising a tubular end cap removably received over the periphery of the end of said second housing portion.

7. The invention as defined in claim 6 wherein said end of said second housing portion includes a reduced cross-sectional, peripheral portion which defines an abutment surface and wherein an axial end of said end cap rests against said abutment surface.

8. The invention as defined in claim 7 wherein said tubular end cap is axially longer than said reduced cross-sectional, peripheral portion.

9. The invention as defined in claim 3 wherein said first means comprises a second axially extended portion of said handle, wherein said second portion of said handle is cylindrical and peripherally dimensioned substantially the same as the narrowest portion of said first portion of said handle.

10. The invention as defined in claim 1 and in which said handle is tapered with a reduced diameter at its outer end and to facilitate disengagement with said tubular housing.

11. The invention as defined in claim 4 and further comprising a second tubular cap removably received over the periphery of the end of said second housing portion.

12. The invention as defined in claim 6 and further comprising fluid passage means intermediate the periphery of said housing and said tubular cap for enabling air to communicate between the interior and exterior of said housing during sterilization.

13. The invention as defined in claim 4 and further comprising fluid passage means intermediate the periphery of said housing and said tubular cap for enabling air to communicate between the interior and exterior of said housing during sterilization.

14. The invention as defined in claim 11 and further comprising fluid passage means intermediate at least one of said tubular end caps for enabling air to communicate between the interior and exterior of said housing during sterilization.

15. The invention as defined in claim 3 wherein said first portion of said handle is conical.

16. An acupuncture needle and needle guide assembly comprising:

a needle, an elongated handle having a first axial portion secured to one end of said needle, an open ended tubular housing having a first portion with a tapered inner bore which is dimensioned to frictionally engage said first portion of said handle and a second elongated portion adjacent said first bore portion and dimensional to enclose said needle therein, first means for manually, slidably displacing said handle in a direction toward said second portion of said housing, at least one tubular end cap covering an end of said tubular housing and, fluid passage means intermediate said at least one tubular end cap and said housing for enabling air to communicate between the interior and exterior of said housing during sterilization.

* * * * *